US006575903B1

(12) United States Patent
Collins (10) Patent No.: US 6,575,903 B1
(45) Date of Patent: Jun. 10, 2003

(54) BREAST SELF-EXAMINATION ALARM AND DATA LOGGING APPARATUS

(76) Inventor: Shelia Collins, 1634 Fiske Ave., Pasadena, CA (US) 91104

( * ) Notice: Subject to any disclaimer, the term of this patent is extended or adjusted under 35 U.S.C. 154(b) by 0 days.

(21) Appl. No.: 10/039,523

(22) Filed: Jan. 4, 2002

(51) Int. Cl.[7] .......................... A61B 5/00; G06F 15/04; G06F 15/02; G06F 19/00
(52) U.S. Cl. ...................... 600/300; 128/897; 128/920; 702/19; 708/131
(58) Field of Search .............................. 600/300–301, 600/551, 549, 587, 557; 128/903, 904, 920, 898, 897; 705/2–4; 702/19, 33, 127; 708/105, 109, 112, 131; 450/1; 340/573.1; 700/11, 16, 90

(56) References Cited

U.S. PATENT DOCUMENTS

| 5,016,917 | A | 5/1991 | Dubner |
| 5,020,671 | A | 6/1991 | Smith |
| 5,207,582 | A | 5/1993 | Michelson |
| 5,381,077 | A | 1/1995 | McGuire |
| 5,657,753 | A | 8/1997 | Jacober |
| 6,364,834 | B1 * | 4/2002 | Reuss et al. ................. 600/300 |

OTHER PUBLICATIONS

Aladdin Communicatons, "pPatrol TM Instructions", Dec. 19, 2002, pp. 1–5, Copyright Oct. 2002.*

* cited by examiner

*Primary Examiner*—Max F. Hindenburg
*Assistant Examiner*—Michael Astorino
(74) *Attorney, Agent, or Firm*—Goldstein & Lavas, P.C.

(57) ABSTRACT

An alarm and data logging apparatus for reminding, encouraging, and electronically recording results of regularly scheduled preferably monthly breast self-examinations (BSEs). The apparatus includes a computer with a calendar/clock circuit or equivalent software functions, along with a human-interface. The computer is configured for determining via the calendar/clock when a pre-defined alarm time and date has been reached. An alarm is issued in a repeating yet reasonable fashion until the woman to which the alarms are issued conducts a BSE and records the results of the BSE into the apparatus. The apparatus supports the archiving of results in a database of the computer or a database of a remote computer located at a remote location.

12 Claims, 8 Drawing Sheets

BREAST SELF-EXAMINATION ALARM AND DATA LOGGING APPARATUS

TECHNICAL FIELD

The present invention relates to alarm and data logging apparatus. More particularly, the invention relates to a preferably self-contained apparatus for issuing alarms and recording the results of regularly scheduled breast self-examinations, conducted by a woman at a pre-determined optimum time each month.

BACKGROUND ART

The incidence of breast cancer has reached near epidemic proportions in certain areas of the world. In the United States breast cancer in woman is among the most commonly discovered malignant tumor, and it is the leading cause of death by cancer. In several regions of the world, a significant increase has been documented wherein at least 1 woman in 10 will have a breast cancer related event before the age of 60.

Importantly, researchers have determined that the earlier cancer is detected, the smaller the size of the discovered tumor, and the greater the number of years one can expect to be cancer free. Simply put, early detection leads to a greatly increased survival rate and subsequent cancer-free life span.

At present, there are a number of well known and accepted methods available for detecting and diagnosing breast related abnormalities. For example, the ubiquitous mammography, which is an x-ray based imaging technique, is employed by large numbers of woman on a regular annual or semi-annual basis. Also, recently improved sonar based imaging apparatus are also utilized. Each of these techniques involves an imaging of a woman's breasts to aid in detecting small, possibly non-palpable, lumps and abnormalities.

Many doctors also strongly recommend that woman perform regular monthly breast self-examinations. Self-examinations are particularly desirable for woman with a history of breast cancer and pre-cancer related events, as an abnormality may be discovered months before a next periodic imaging (e.g., mammography) appointment. Breast self-examination (BSE) represents a simple, fast, and inexpensive method, easily performed at home or in a private setting, that enables early detection of lumps, tumors, and other abnormalities. It has been documented that 10 to 15 percent of palpable tumors fail to be detected by mammography. In addition, when considering women who conduct BSE frequently, say on a monthly basis, the size of detected tumors has been determined to be significantly smaller (by almost 50%) than those women who don't regularly perform BSE.

Even with all of the above known and well understood by most women, many would attest to the difficulty of performing BSE on a truly regular and consistent basis. First, BSE is best performed 7 to 10 days after the conclusion of a woman's menstrual cycle. This is much more difficult to remember and time than if the BSE was best conducted during the menstrual period. In addition, even if the BSE is performed, most women don't record important information related to possible breast abnormalities, and where they were detected. Should an abnormality be detected, it is not unusual for a woman to delay one or more months before contacting their Doctor. A natural 'denial' period can be expected in many women. As a result, time and information, which may prove helpful to a physician, is lost!

Accordingly, it would be most desirable to have an apparatus, which may most preferably be fully self-contained, that enables a quick and easy programming so as to remind a woman to perform BSE at an appropriate time of each month. The apparatus would be structured to enable quick and easy recording and archiving of the results of each BSE performed periodically over a long period of time. A number of other characteristics, advantages, and or associated novel features of the present invention, will become clear from the description and figures provided herein. Attention is called to the fact, however, that the drawings are illustrative only. In particular, the embodiments included and described, have been chosen in order to best explain the principles, features, and characteristics of the invention, and its practical application, to thereby enable skilled persons to best utilize the invention and a wide variety of embodiments providable that are based on these principles, features, and characteristics. Accordingly, all variations possible are contemplated as being part of the invention, limited only by the scope of the appended claims.

SUMMARY OF THE INVENTION

In accordance with the present invention, an apparatus for issuing alarms and recording results of regularly scheduled breast self-examinations (BSE) is provided. Importantly, the apparatus is intended to remind and encourage that BSE be performed by a woman during a pre-determined optimal temporal interval of each of a succession of months. It may be noted that a pre-determined temporal interval is calculated and determined for each of a plurality of months using information provided by the woman during a setup and initializing of the apparatus, or information later provided, for example, at the start of a menstrual cycle.

The apparatus is configured with a controller or a computer including a portion for determining the present time and date, which has also been termed a 'temporal moment'. For example, the computer may include an electronic circuit, or equivalent software functions, that provide for a calendar/clock function. The calendar/clock enables the computer to determine when a pre-selected temporal moment has been reached. That is, to determine when a BSE is due to be conducted. The apparatus is further structured with a human interface that is operatively and functionally coupled to the computer. The human interface enables, among other functions, an exchanging of information with one or more women related to the setting up and initializing of the apparatus, as well as the issuing and responding to alarms related to temporal intervals during which a BSE is to be performed.

Another aspect of the apparatus provides for a database, preferably provided by and/or supported by the computer. Alternately, a remote computer to which a link may be established may provide access to a suitable database. In any possible situation, the database is available to a processor of the computer and structured to enable the computer to determine when a pre-selected temporal interval for each month has been reached so as to support the issuing of the above mentioned alarms. The human interface may be structured to include at least one of an audio module, for providing audio information to the woman including one of audio tones and voice alarms, and a vibration unit that may be energized by the computer for providing a substantially silent alarm to the woman, as required. It may be noted that the terms 'month', 'monthly', and equivalents, are intended to be broadly defined as a repeating periodic interval, possibly having a period that varies slightly, and repeats. Therefore, a monthly interval, as determined by a woman's actual menstrual cycle may actually be less than or greater than 30 days for a given cycle/month.

The human interface would most preferably include means that readily enables a woman to update previously input information. For example, the updated information may include, among other items, at least one of a starting date of a past or present menstrual cycle, a duration of an actual past or present menstrual cycle, an average number of days before the start of a next menstrual cycle, etc. Such an updating of these items may be applied for calculating, updating, and storing for future use, a variety of alarm dates at which time an alarm is to be issued to the woman indicating that a self-examination is to be conducted.

An important aspect of the present invention is that during a setting up of the apparatus a woman may provide actual information based on one or more past menstrual cycles, or estimated information when actual exact dates, etc., are not known or available. In addition, the woman may input a combination of actual and estimated information. When considering this feature, an 'update' command, for example one similar to that taught by Jacober et al., in U.S. Pat. No. 5,657,753, may be employed. Such a feature would enable a woman to correct or re-align the calculated alarm dates, including the next alarm to be issued, based on an unexpected early or delayed start and or end of a menstrual cycle. However, the present apparatus will enable a somewhat detailed and archived record of each of a succession of breast self-examinations performed to be available to individuals, even years after they are conducted. This archiving and long term storage of results is an important feature supported by embodiments of the invention.

BRIEF DESCRIPTION OF THE DRAWINGS

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows.

| Partial List Of Reference Numerals | |
|---|---|
| 10, 10a | (alarm and data logging) apparatus |
| 12 | housing or case |
| 20 | computer |
| 22 | processor (or control logic) |
| 24 | memory/storage |
| 24a | database (local) |
| 24b | database (remote) |
| 26 | calendar/clock circuit or function |
| 28 | interface circuitry (as required) |
| 30 | human interface |
| 32 | display unit |
| 36 | user input means |
| 36a | direction keys (up, down, left, right) |
| 36b | ESTIMATED/ACTUAL keyswitch |
| 36c | MENU pushbutton (PB) |
| 36d | ENTER pushbutton (PB) |
| 36e | Keypad |
| 38 | audio module |
| 38a | audio output transducer |
| 38b | volume control |
| 42 | vibration unit |
| 44a | SETUP PROMPTS switch |
| 44b | ALARM SELECT switch |
| 50, 50a | operative coupling |
| 60 | remote link |
| 70 | communications module |
| 70a | antenna |
| 76 | remote computer (w/database) |

DETAILED DESCRIPTION OF EMBODIMENTS OF THE INVENTION

Figure 1:
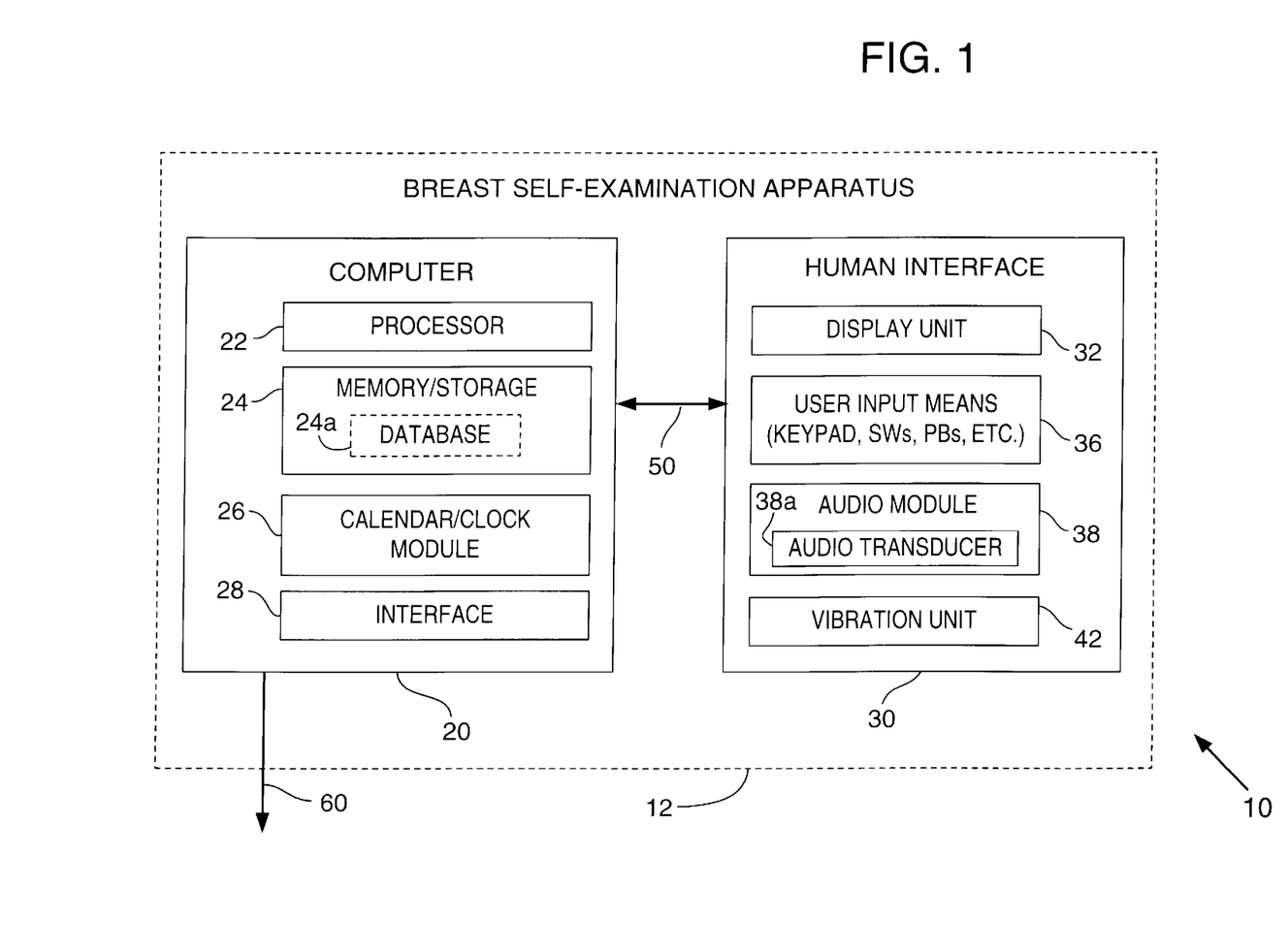
FIG. 1 is a high level block diagram of a first preferred embodiment of a breast self-examination alarm and data logging apparatus in accordance with the invention.

Referring now to the drawings, FIG. 1 depicts an embodiment and apparatus in accordance with the invention. The apparatus 10 is an alarm issuing and data logging instrument structured for issuing alarms and recording, preferably electronically, the results of regularly scheduled breast self-examinations conducted by a woman. The apparatus 10 issues alarms based on information, which may be actual information and or estimated information, during each of a plurality of periodic (e.g., monthly) pre-determined, optimal temporal intervals. It may be noted that the invention is preferably embodied as a self-contained, compact, and very easy to carry device. However, it must be understood that a most preferable embodiment of apparatus 10 enables a woman to fully indicate and input results associated with abnormalities, and further may be arranged to provide immediate recommendations to the woman based on results indicated. This aspect of the invention will be discussed more fully hereinafter.

As is well understood by skilled persons, it is strongly recommended that a woman conduct breast self-examinations, as close to a fixed period of time or an equal number of days after a woman completes a menstrual cycle. For example, such a preferred temporal interval may be established to begin 7 days after the completion of a most recent menstrual cycle and run for 5 to 7 days therefrom. Accordingly, the apparatus 10 includes a computer 20 to, among other functions, determine when an optimal temporal interval has been reached, and a human interface 30 that supports, among other functions, the issuing of alarms to the woman. Each alarm, which may best be thought of as an alarm event composed of a plurality of repeating alarms, is issued for indicating the need to perform a breast self-examination (BSE) and immediately record results of the self-examination after or as it is being conducted.

Figure 3:
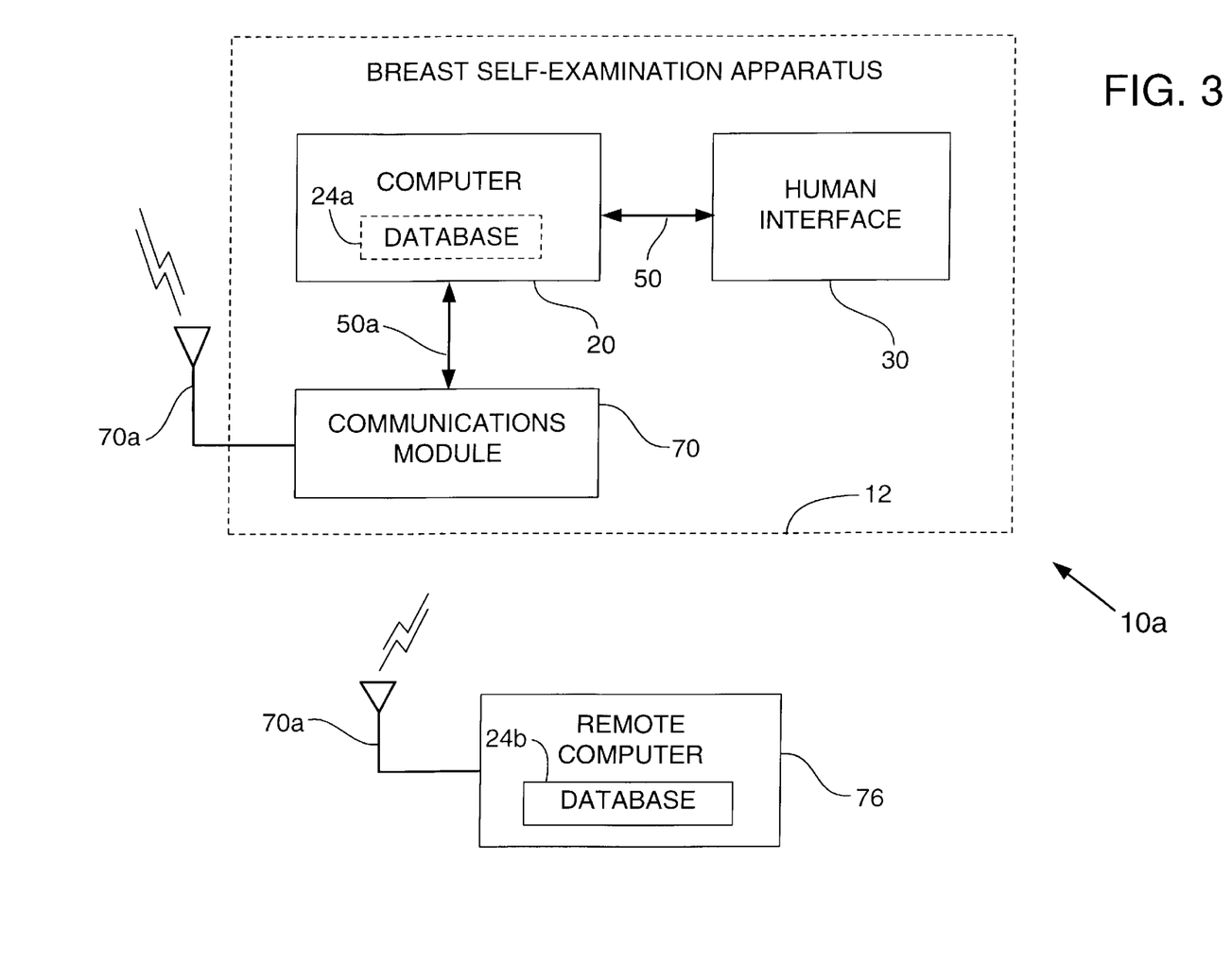
FIG. 3 is a high level block diagram of another preferred embodiment of the invention.

The computer 20 of FIGS. 1 and 3 is included for a number of other computing and control functions, including the function of determining a present time and date. This function may be realized by including a calendar/clock circuit, utilizing timer-counter hardware, and or using a software function. Regardless of how a time-date tracking function is implemented, the computer is configured for determining when an alarm is to be issued to a woman who owns or employs the apparatus 10. As illustrated in FIG. 1, preferred embodiment of the computer 20 may be structured with a processor 22, a memory/storage subsystem 24 that may be embodied to support or contain a database 24a, a calendar/clock module 26, and any required interface circuitry 28. It may be noted that many or all of these components of computer 20 may be provided by well known single chip solutions, including micro-controllers and large programmable devices such as field programmable gate arrays (FPGAs) and application specific integrated circuits (ASICs).

Returning to FIG. 1, the apparatus 10 further includes the human interface 30, which is operatively coupled to the computer 20 by way of link 50, and structured for exchanging information with the woman. This information may be employed for setting up and initializing the apparatus 10, as well as determining a proper time for issuing alarms and prompts. For example, some of the information that may be exchanged with the woman may include the following:

a) a starting date of a pastor present menstrual cycle;
b) a duration of a past or present menstrual cycle; and
c) an average number of days before the start of a next menstrual cycle;
d) a present time and or date;
e) a plurality of preferred times during an alarm or alarm event each discreet alarm is to be sounded (e.g., 7 AM, 3 PM, 7 PM and 10 PM);
f) other information that is useful for calculating, updating, and storing alarms for issuing to the woman when a breast self-examination is to be conducted;
g) information that is useful for indicating, updating and or storing results of a respective BSE;
h) selecting the types of prompts that may be issued during setup and initialization, and subsequent operation of the apparatus 10.

Figure 2:
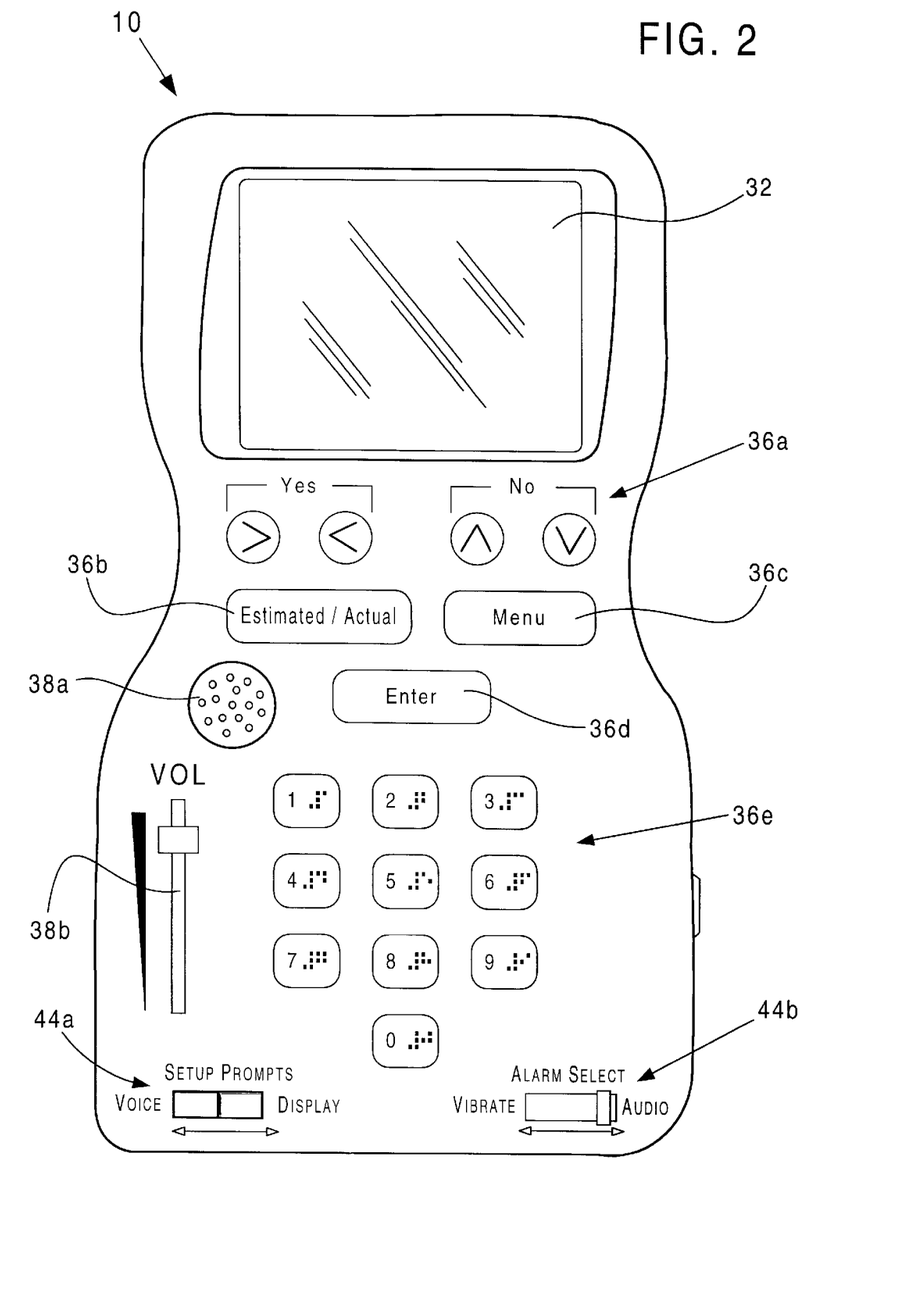
FIG. 2 provides a plan view of an embodiment of a housing and a preferred user interface panel consistent with the embodiment of FIG. 1.
Figure 4:
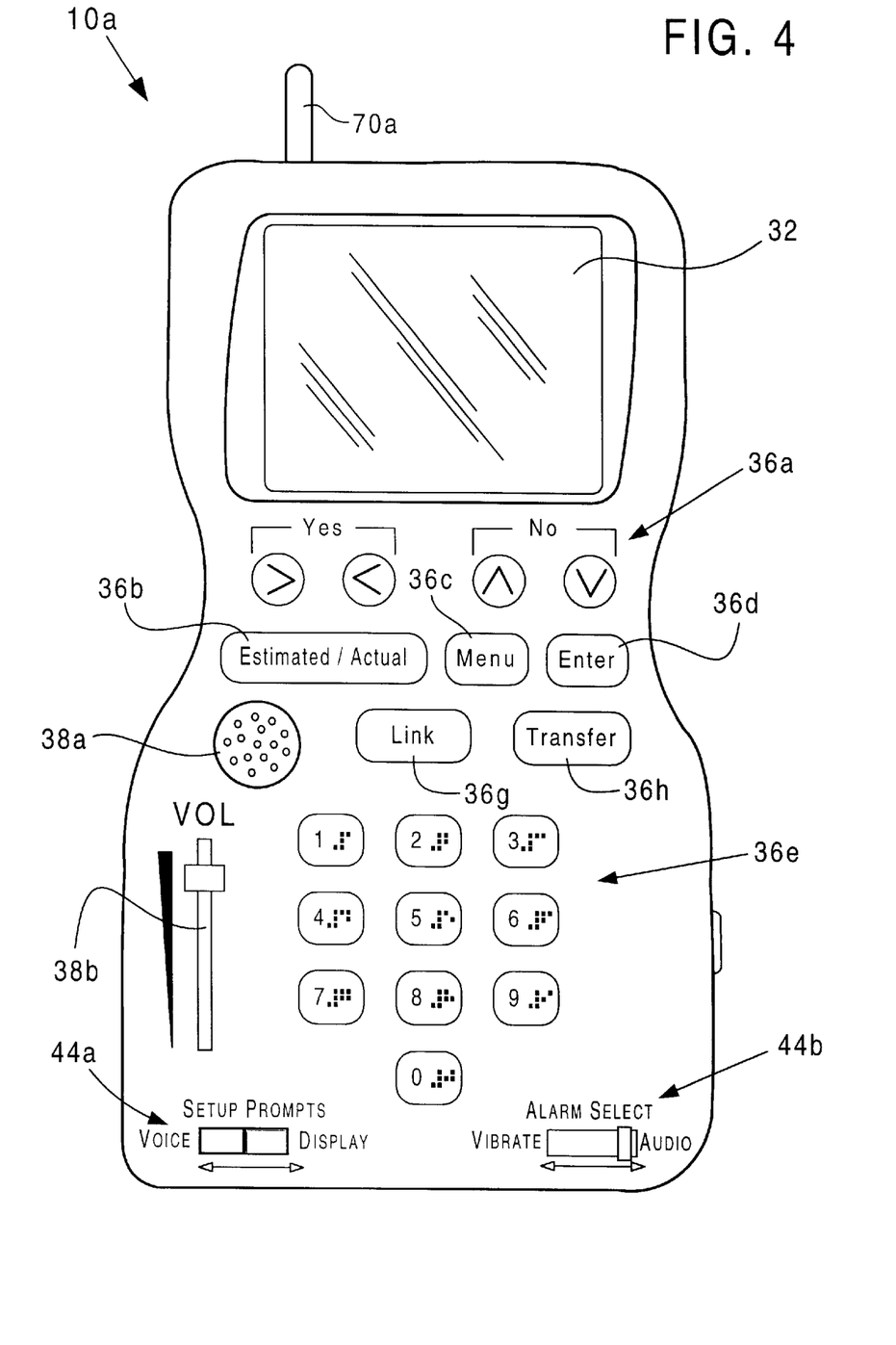
FIG. 4 illustrates a plan view of an embodiment of a housing and a preferred user interface panel consistent with the embodiment of FIG. 3.

As such, and as illustrated in FIGS. 2 and 4, the human interface 30, will preferably include a plurality of user input means 36 such as key switches and pushbuttons (key buttons). These may most preferably include a keypad 36e, and positioning keys 36a, a menu PB 36c, an enter PB 36d. Other possible human interface input devices may include a volume slider 38b, and maintained switches 44a and 44b. As illustrated, a switch 44a may be provided to select the type of setup prompts employed during setup and initialization, while the switch 44b may be provided for selecting the form of alarms to be issued. As skilled persons will appreciate, embodiments of the human interface 30 may certainly be provided wherein menu based selections for the type of prompts or alarms may be displayed upon the display 32 and selected using one or more position keys 36a, and an ENTER key 36d. Accordingly, the switches 44a and 44b may not be required. In addition, the apparatus 10 of the invention may include means such as pushbuttons, etc., for readily enabling a woman to update previously input information including at least one of a starting date of a past or present menstrual cycle, a duration of an actual past or present menstrual cycle, or an average number of days before the start of a next menstrual cycle. The woman may readily update this information via menus that may be accessed by pressing the MENU button 36c shown in FIGS. 2 and 4. Alternately, the display 32 may be provided as a common touch screen that readily enables a woman to input and or update information. It should be noted that it is certainly possible to provide embodiments of the invention having other means for supporting the inputting of information from the user and the delivering of alarms and other information to the user. Accordingly, preferred embodiments of the invention, including those depicted in FIGS. 1 through 4, maybe structured with at least one of an audio module 38 for providing audio information to the woman including one of audio tones and voice alarms. The tones and voice alarms may be issued for indicating the start of the temporal interval, as well as functions to support voice-command recognition, and voice related inputting of results of an examination. When an audio module is included a small speaker 38a would preferably be included. In addition to the audio module, the apparatus 10 may be embodied with a vibration unit 42 that may be energized by the computer for providing a substantially silent alarm to the woman indicating the start of the optimal temporal interval. This function may support private reminders that a breast self-examination is to be conducted.

Importantly, the present invention and apparatus 10 includes a database 24a for storing alarm information and BSE results information. Once a woman has input information during setup (as discussed above), the computer 20 may be employed for calculating, updating, and storing a plurality of alarms within the database. The database is also available for recording, storing, and archiving results of each breast self-examination conducted. A link 60 may be included for supporting an exchange of information between the apparatus 10 and other remote systems. For example, as can be seen in FIG. 3, embodiments of the invention may be provided with the database, or a significant portion thereof, remotely located. Such a system architecture would preferably include a remote computer 76 having a database 24b. The apparatus 10 and the remote computer 76 may be linked by any suitable link or communication channel, including common wireless links that may be supported by the antennas 70a. When the apparatus 10 includes a communication module 70, or equivalents thereto, information entered by a woman may be downloaded to a remote location for review by authorized individuals. For example, after a breast self-examination is performed, the apparatus 10 may automatically, or as a result of prompts and key presses provided to the woman, transfer the results to a remote location for review and analysis by a medical professional such as a nurse or doctor. The results information may also be analyzed by the apparatus 10, with recommendations made directly to the woman. For example, such recommendations may be provided to the woman indicating an appointment should be made with a doctor.

Figure 5:
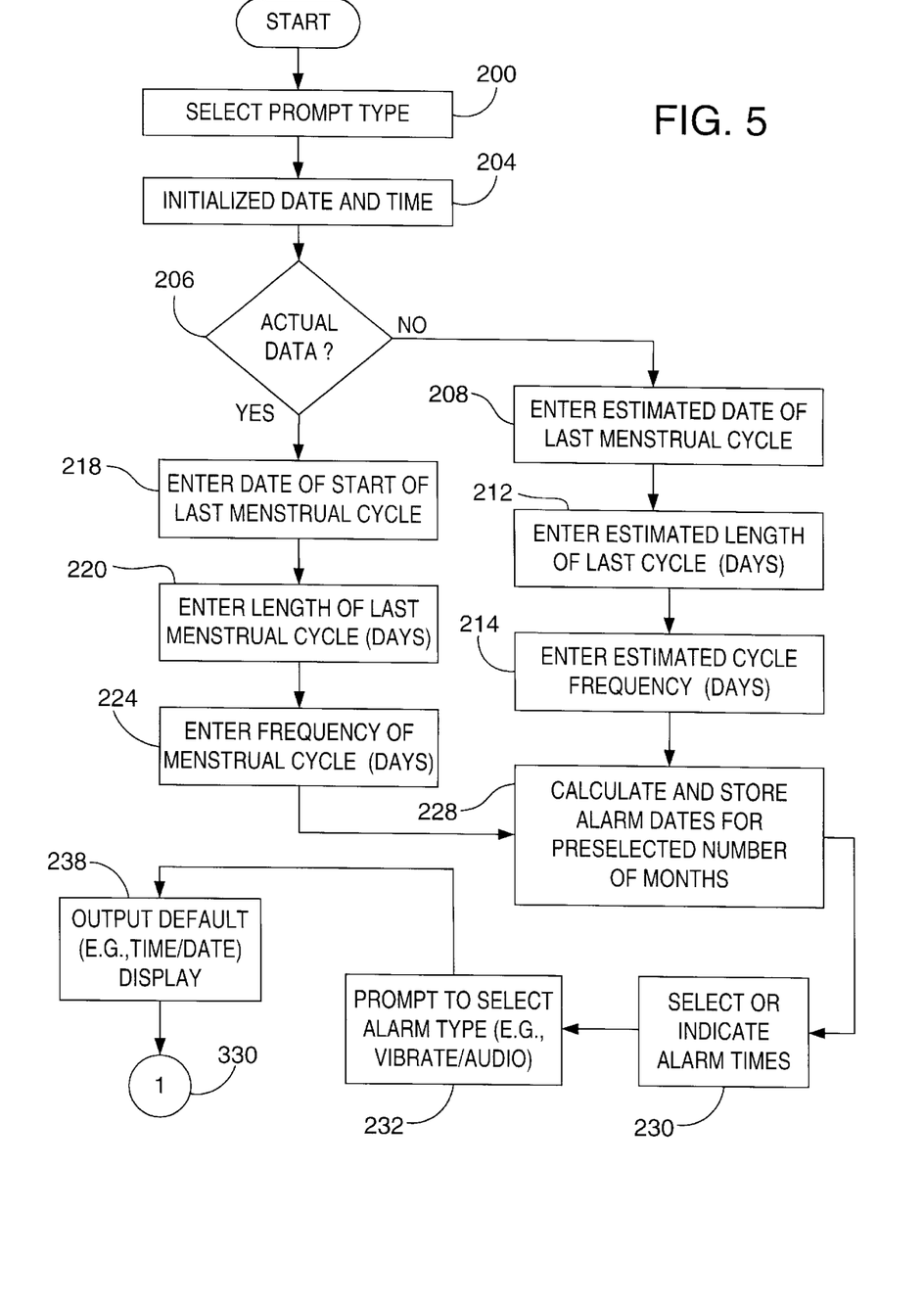
FIG. 5 is a high level flowchart of one possible setup and configuration method employable with the apparatus of FIGS. 1 through 4, and equivalents thereto.

Referring now to FIG. 5, one possible method for setting up and initializing the apparatus 10 will be discussed. At 200 a user may select a prompt type. Prompts may be provided by voice, audio tones, a displaying of text or symbols, or a combination thereof. At 204, the date and time may be set. Next, at 206 an indication is provided as to whether data (e.g., dates, etc.) to be input will be actual data or estimated data. If the data is to be actual data, at 218 an actual starting date of the last menstrual cycle is input. At 220, an actual length of a most recent menstrual cycle is entered. Finally at 224 the frequency or number of days between menstrual cycles (based on past cycles) may be entered.

If at 206, an operator or the woman indicates that the information to be entered is estimated, at 208 an estimated starting date is input, at 212 an estimated length of each cycle is entered, and at 214 an estimated frequency or number of days between cycles is entered. It should also be noted that methods of the invention are contemplated to enable a combination of actual and estimated information to be entered (not illustrated).

As indicated in FIG. 5, regardless of whether actual or estimated information is input, at 228 calculations are made based on the input information to determine the optimal temporal intervals during which breast self-examinations are to be performed—for each of a succession of months. These calculation may provide for the determining of alarm dates for a plurality of consecutive months. For example, a years worth of dates may be calculated and stored. Once the dates have been calculated, at 230 preferred, pre-determined, or selected times during a day that alarms are to be issued may be established. For example, the apparatus 10 may provide default times to issue alarms. These may include a plurality of pre-defined times such as 7 AM, 3 PM, 7 PM, and 10 PM. Alternately, the woman setting up the apparatus 10 may be able to select, input, or alter alarm times.

It must be understood that the terms 'month', 'monthly', and equivalents employed herein, are intended to be broadly defined as a repeating periodic interval, possibly having a cycle that varies slightly. For example, a monthly interval for a respective woman, may actually be less than or greater than a 30 day interval for a given cycle/month. Therefore, it is contemplated that the term monthly be broadly defined and the actual corresponding number of days vary to match the woman's own periodic cycle.

Returning to FIG. 5, at 232, a type of alarm to be issued is selected. The alarm types may include audio tones, voice messages, vibration alerts, etc. Once the apparatus 10 has been fully setup and initialized, a default display arrangement may be displayed on the display 32. A preferred default, non-alarm display layout may provide items such as the present time, present date, date of the next alarm, etc. Once the default display is presented at 228, control may be transferred to an operating method, as illustrated in FIGS. 6A and 6B.

Figure 6A:
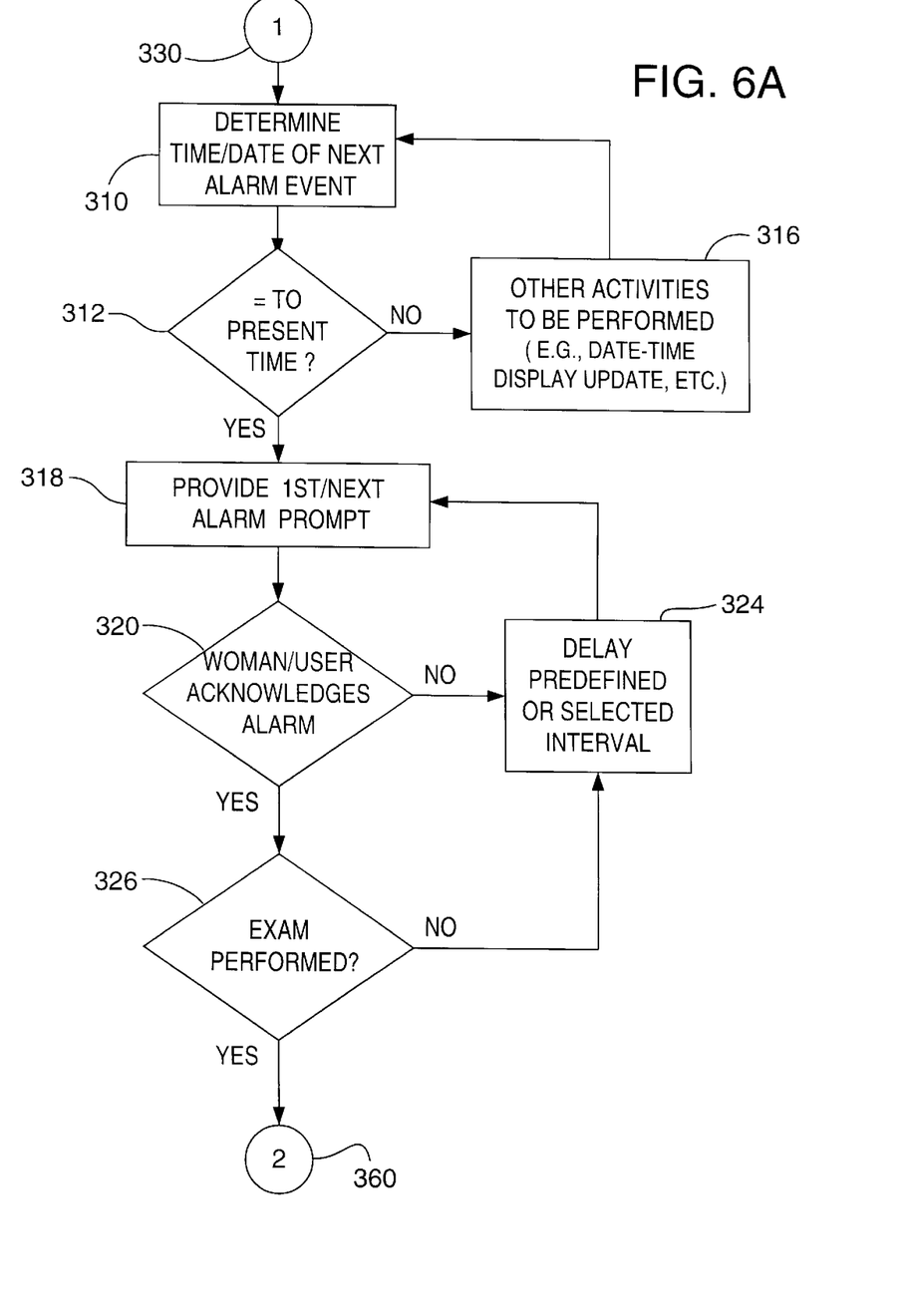
FIGS. 6A and 6B provide one of a number of possible preferred operational methods for a variety of embodiments of the invention.
Figure 6B:
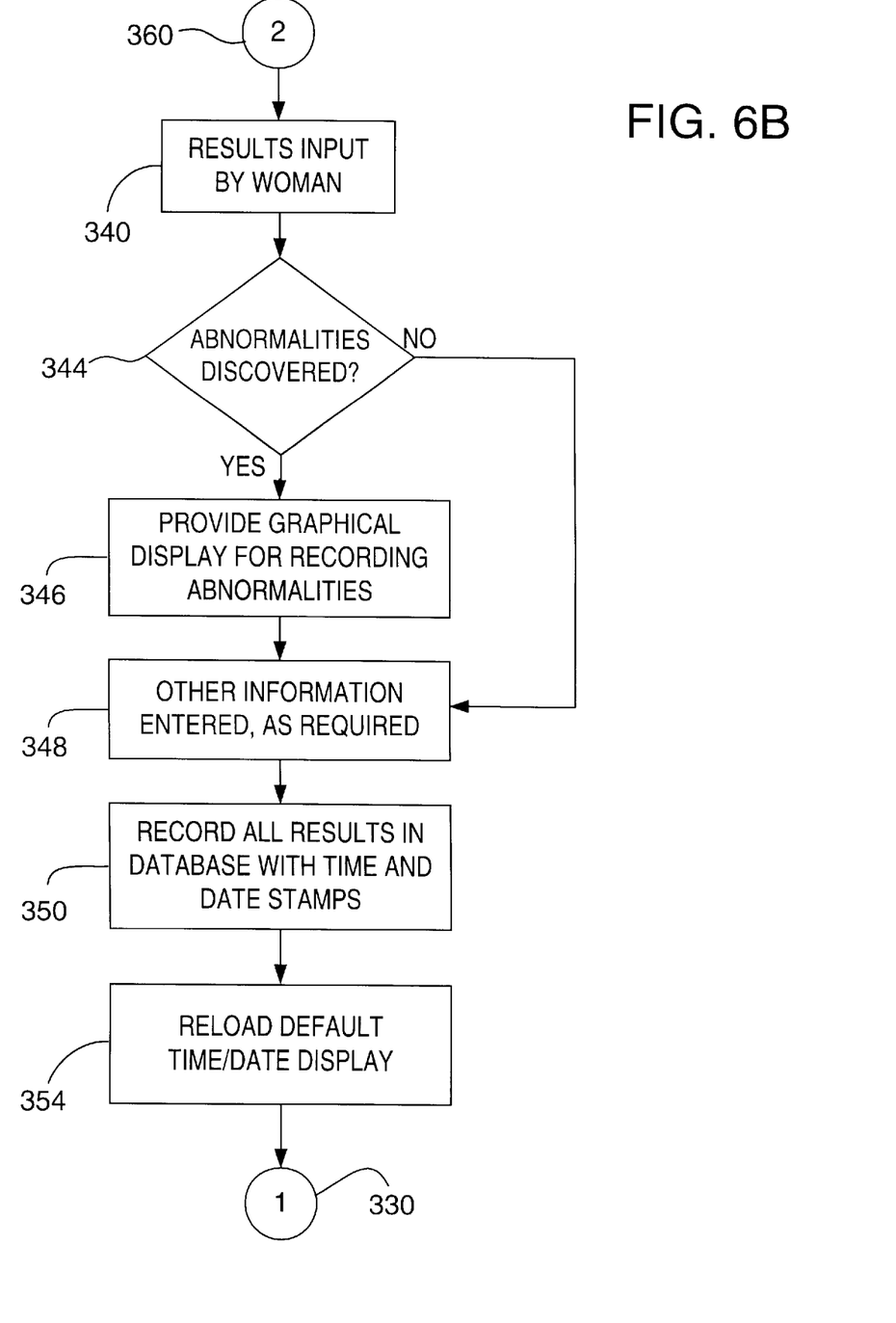

Turning to FIGS. 6A and 6B, an embodiment of a simplified and somewhat fundamental operating method is depicted. The entry at 330 assumes that the woman or another suitable individual has completed setting up and initializing the apparatus 10. At 310, the computer 20 determines the present time and date, and checks to see if an alarm is to be issued at 312. If at 312 it is determined that the present time is not equal to a time that an alarm is to be issued, 316 may provide for other 'background' activities, such as updating information being displayed on display 32. After 316, a check of the present time is again made, with steps 310, 312, and 316 repeating until the present time corresponds to an alarm time. Once an alarm time is reached, a first/next alarm prompt is issued at 318.

At 320, a user (e.g., the woman) acknowledges the alarm. An actual acknowledging by the user may be realized indicating one of several possible actions. First, if the woman can not perform the breast self-examination at the time the alarm is issued, the woman may respond by inputting or selecting a request for another alarm to be issued at a later time. The alarm may not simply be disabled or cancelled. For example, the woman may request the alarm be reissued a selectable number of hours after the present alarm. Alternately, the alarm may be silenced or cancelled with the next alarm issued automatically at some predetermined future time, say 2 or 3 hours after the present time (via delay 324). Regardless of how long the delay at 324 is, a series of alarms may actually be issued before the woman acknowledges the alarm at 320 and indicates that the BSE has been performed at 326. Next at 340, which is shown on FIG. 6B, the woman inputs results of the exam. Results may be indicated in numerous ways including:

a) answering a series of pre-defined questions that may help provide a base line for results of each examination;

b) entering text via an expanded keypad or attachable keyboard;

c) entering a voice recording of results, possibly prompted by displayed or voice prompts;

d) entering text via voice recognition supported by the audio module 38;

e) other available means to input results.

Figure 7:
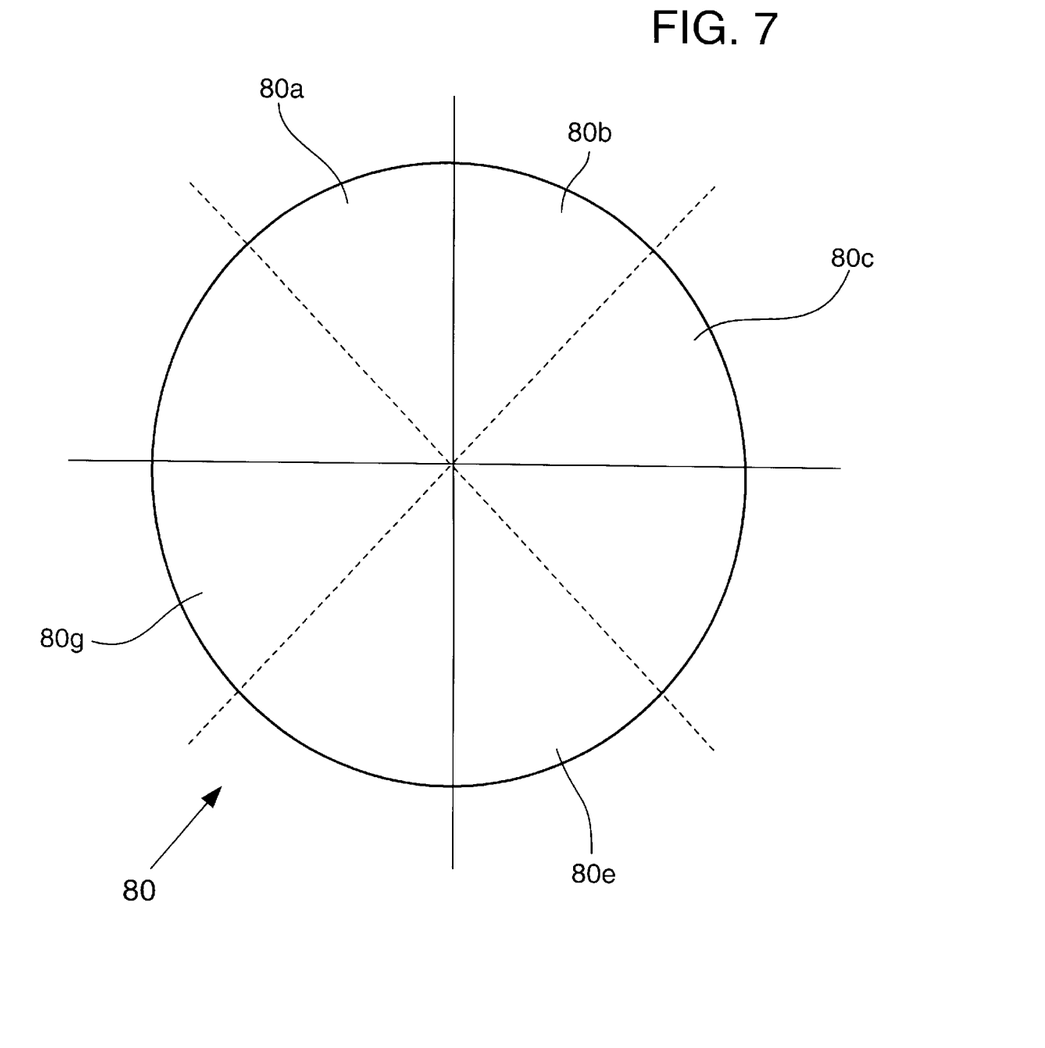
FIG. 7 depicts a preferred graphical representation that may be provided to a woman during and/or after conducting a breast self-examination, which enables a graphical recording of the location, and possibly other information, of any abnormalities that are discovered.

If the woman indicates that abnormalities have been discovered at 344, a graphical display will most preferably be provided for use by the woman in recording and documenting the abnormalities and or findings. For example, as can be seen in FIG. 7, a circular pattern 80 possibly dissected into regions or quadrants, 80a, 80b, etc., may be provided upon the display 32. Alternately, a voice recording may be employed for this purpose. Upon the entering of the information at 346, other information may be entered, as required, at 348. Once all results have been fully entered or finalized, they are stored in an available database. It must be understood that the database may be provided locally as database 24a (see FIG. 1), or remotely as a database 24b provided by a remote computer 76 (see FIG. 3). Returning to FIG. 6b, at 354 a default display possibly including a display of the present time/date information, as well as other information, may be provided.

An additional feature of the invention may provide for an analysis of the results input and associated with each BSE immediately after being stored in the database 24a/24b. The analysis and processing of the results may cause one of a number of actions, possibly including:

a) an issuing of a suggested action, based on the results input, such as a recommendation to contact a doctor or other medical entity. The name of the doctor may have been entered by the woman during setup and initialization of the apparatus 10;

b) a contacting, possibly automatically or with approval of the woman, of a remote location informing a pre-selected authorized individual of the results of the self-examination;

c) an automatic contacting of the woman by an authorized or selected medical individual (such as a doctor, nurse, etc.), after processing and or analyzing the downloaded results.

It may also be noted that the downloaded information may be examined with information uploaded back to the apparatus 10 for viewing by the woman. Downloaded information and data may also be employed to determine a number of items including if suitable alarm dates and times have been determined and or selected, and further that compliance information regarding a conducting of BSEs and an entering of associated results of previously conducted self-examinations has been indicated by the results. Clearly a remote link enables numerous results that have been previously stored to be archived and backed up at the remote site. To support the remote downloading, analysis, and or reviewing of the results entered by the woman, the apparatus 10 must be able to be connected to a suitable remote computer. Such a connection or link may be established by any well known means including a wireless link, an optical link, and or a hardwired link provided by a suitable interconnection cable. Further, as shown in FIG. 4, the human interface 30 may be modified to include additional switches or pushbuttons such as the LINK pushbutton 36g and or the TRANSFER pushbutton 36h. For example, the apparatus 10a may establish a connection when a woman presses the LINK button, and a transfer to a remote computer may be effected by a pressing of the TRANSFER button.

While there have been described herein a plurality of the currently preferred embodiments of the present invention, along with contemplated methods of operation and use, those skilled in the art will recognize that other and further modifications may be made without departing from the invention. For example, if the audio module includes voice command and voice synthesis capabilities, the display 32 may be omitted with only voice and or vibration prompts and alarms issued. In such an embodiment, voice prompts would be followed by keypad inputs or voice responses. Accordingly, the foregoing descriptions of the specific embodiments of the present invention have been presented for the purposes of illustration and description. They are not intended to be exhaustive or to limit the invention to the specific forms disclosed. Obviously numerous modifications and alterations are possible in light of the above teachings. Therefore, it is fully intended to claim all modifications and variations that fall within the scope of the broadly described invention and the appended claims.

What is claimed is:

1. An apparatus for issuing alarms and recording the results of regularly scheduled breast self-examinations performed by a woman during a pre-determined temporal interval of each of a succession of months, the apparatus comprising:
    a) a computer including means for determining a present time and date;
    b) a human interface operatively coupled to the computer and structured for exchanging information with the woman, and as required, with other individuals;
    c) a database available for accessing by the computer to enable the computer to determine when a pre-selected temporal interval for each month has been reached so as to support the issuing of at least one alarm of a plurality of alarms to the woman indicating a start of a temporal interval and a need for a conducting of a breast self-examination;
    d) the database further available for recording and storing information, including information entered by the woman indicating results of the breast self-examination; and
    e) a processor of the computer for processing the results input associated with a present self-examination, causing an action suggestion to be issued to the woman that is based on the results input into the apparatus via the human interface.

2. The apparatus in accordance with claim 1, wherein the computer is employed for calculating and storing each pre-determined temporal interval for each of a plurality of months using information that is:
    a) provided by the woman during a setup and initializing of the apparatus;
    b) provided later, for adjusting a plurality of stored pre-determined temporal intervals.

3. The apparatus in accordance with claim 1, wherein the human interface includes at least one of:
    a) an audio module for providing audio information to the woman including one of audio tones and voice alarms indicating the start of the temporal interval;
    b) a vibration unit that may be energized by the computer for providing a substantially silent alarm to the woman indicating the start of the temporal interval;
    c) means to readily enable the woman to update previously input information including at least one of:
        i) a starting date of a past or present menstrual cycle;
        ii) a duration of a past or present menstrual cycle;
        iii) an average number of days before the start of a next menstrual cycle;
    d) wherein updated information is employable for calculating, updating, and storing alarms for issuing to the woman when a breast self-examination is to be conducted.

4. The apparatus in accordance with claim 3, wherein updated information includes one of:
    a) actual information based on one or more past menstrual cycles;
    b) estimated information entered when actual information is not available;
    c) a combination of actual and estimated information.

5. The apparatus in accordance with claim 4, wherein the human interface is structured such that the woman can update estimated information with actual information including at least one of:
    a) an actual starting date of a next menstrual cycle;
    b) an actual length of a menstrual cycle;
    c) an actual interval between menstrual cycles;
thereby causing a re-calculating and updating of future alarm events based on actual information.

6. The apparatus in accordance with claim 1, wherein a plurality of pre-selected times associated with an issuing of alarms for a temporal interval are provided by the woman via the human interface.

7. The apparatus in accordance with claim 1, wherein the issuing of a present alarm may be followed by the woman inputting a request for another alarm to be issued a selectable number of hours after the present alarm.

8. The apparatus in accordance with claim 7, wherein for each of a plurality of issued alarm, the woman may respond by inputting a request for another alarm to be later issued.

9. The apparatus in accordance with claim 1, wherein the database is contained within a memory structure of the computer, with the apparatus structured as a fully self-contained unit.

10. The apparatus in accordance with claim 1, wherein the apparatus further includes a wireless link to a centralized remote database, with the database containing at least the information and results associated with the woman.

11. The apparatus in accordance with claim 1, wherein the information includes at least one of:
    a) alarm dates and times;
    b) compliance information regarding an entering of results of previously conducted self-examinations;
    c) archived results of previous self-examinations.

12. The apparatus in accordance with claim 1, wherein the information is accessible for recalling and reviewing.

* * * * *